(12) United States Patent
Vaynovsky et al.

(10) Patent No.: US 6,306,101 B1
(45) Date of Patent: Oct. 23, 2001

(54) ELECTRONIC DEVICE FOR MEASURING SENSORY THRESHOLDS IN HUMANS AND ANIMALS

(75) Inventors: Barney Vaynovsky, Woodland Hills; Ingrid Vaynovsky; Thomas C. Delahanty, both of Thousand Oaks; Gregory Vaynovsky, Encino, all of CA (US)

(73) Assignee: IITC Inc., Woodland Hills, CA (US)

( * ) Notice: Subject to any disclaimer, the term of this patent is extended or adjusted under 35 U.S.C. 154(b) by 0 days.

(21) Appl. No.: 09/549,476

(22) Filed: Apr. 14, 2000

(51) Int. Cl.[7] ................................................. A61B 19/00
(52) U.S. Cl. ......................................................... 600/557
(58) Field of Search ..................................... 600/552, 553, 600/554, 555, 556, 557

(56) References Cited

U.S. PATENT DOCUMENTS

| | | | |
|---|---|---|---|
| 3,662,744 | * 5/1972 | Low et al. | 600/557 |
| 5,673,703 | * 10/1997 | Fisher et al. | 600/552 |
| 6,113,551 | * 10/2000 | Isaacs et al. | 600/557 |

* cited by examiner

*Primary Examiner*—Eric F. Winakur
*Assistant Examiner*—Pamela Wingood
(74) *Attorney, Agent, or Firm*—Thomas I. Rozsa; Tony D. Chen; Jerry Fong

(57) ABSTRACT

An apparatus for testing and measuring sensory thresholds in humans and animals, including an electronic algometer and a probe housing. A strain gauge is installed within the probe housing and having one end fixed thereto and the other end movable. A support member is attached to the movable end of the strain gauge and extends out from an opening on the probe housing. A pipette member is press-fitted to the support member, where a resilient string has one end attached to the pipette member and the other end has a uniform tip diameter for creating a uniform reaction when a force is exerted thereto. The strain gauge measures the amount of deflection responsive to the force applied from the nylon string onto the support member with the uniform tip diameter of the resilient string in contact with the skin area of the human or animal and generates an electrical output signal indicative of the pressure applied. The electronic device is electrically interconnected to the strain gauge for receiving the electrical output signal from the strain gauge.

54 Claims, 3 Drawing Sheets

ELECTRONIC DEVICE FOR MEASURING SENSORY THRESHOLDS IN HUMANS AND ANIMALS

BACKGROUND OF THE INVENTION

1. Field of the Invention

The present invention generally relates to devices for measuring sensory thresholds in humans and laboratory animals. More particularly, the present invention relates to electronic devices for testing and measuring sensory thresholds in humans and laboratory animals.

2. Description of the Prior Art

Specifically, devices for testing and measuring sensory thresholds of humans and laboratory animals are well known in the art. These prior devices use nylon lines or stiff pins. The disadvantage with prior art devices is that they are sensitive to humidity and ambient temperature. The prior art devices consist of acrylic thin handles, into the end of which a nylon string is mounted by permanent means. For all the different resiliences required, there are about 19–20 different nylon string thickness with their 19–20 plastic handles. Each handle has a force resiliency marked on it. This imprinted number is the only data available to the user or scientist. Although it is a fact, that a 15% relative humidity change can change the exerted force by 40%, the user had to believe that this number is constant. There was no means to reliably measure the change due to these factors. There is a 20–30% change in force depending on the degree of bending. In some cases due to relative humidity some nylon strings exhibit over 100% change in force with 26% relative humidity change.

It is highly desirable to have a very efficient and also very effective design and construction of an electronic algometer for testing and measuring sensory thresholds in humans and laboratory animals. It is desirable to provide an electronic algometer with a resilient pressure sensitive probe, where the resilient pressure sensitive probe is not sensitive to the degree of bending, humidity and ambient temperature. It is also desirable to provide an electronic algometer with a resilient pressure sensitive probe, where the probe has a uniform tip diameter which creates a uniform reaction when the force is exerted thereto.

SUMMARY OF THE INVENTION

The present invention is an apparatus for testing and measuring sensory thresholds in humans and animals.

The apparatus includes an electronic algometer that has a probe housing which houses a strain gauge. The strain gauge has a fixed end and a movable end. A rigid support member is attached to the movable end of the strain gauge and extends out from an opening on the probe housing. A pipette member is press-fitted to the rigid support member. A resilient nylon string or nylon-monofilament has one end attached to the pipette member and the other end has a flexible uniform tip diameter for creating a uniform reaction when a force is exerted thereto. The strain gauge measures the amount of deflection responsive to the force applied from the nylon string onto the rigid support member with the uniform tip diameter of the nylon string in contact with the skin area of the human or animal and produces an electrical output signal indicative of the pressure applied. The electronic algometer is electrically interconnected to the strain gauge for receiving the electrical output signal from the strain gauge. The electronic algometer includes a readout display for displaying the pressure sensed by the strain gauge, where the electronic algometer accurately displays the pressure applied by the uniform tip diameter of the nylon string on the skin area of the human or animal.

It is an object of the present invention to provide an improved electronic algometer which employs a resilient nylon string made of any suitable material as a pressure sensitive delivering element.

It is an additional object of the present invention to provide an improved electronic algometer which employs a resilient nylon string having a uniform diameter and a uniform tip diameter which creates a uniform reaction when a force is exerted thereto.

It is a further object of the present invention to provide an improved electronic algometer which employs a resilient nylon string which is not sensitive to the degree of bending, humidity and ambient temperature.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
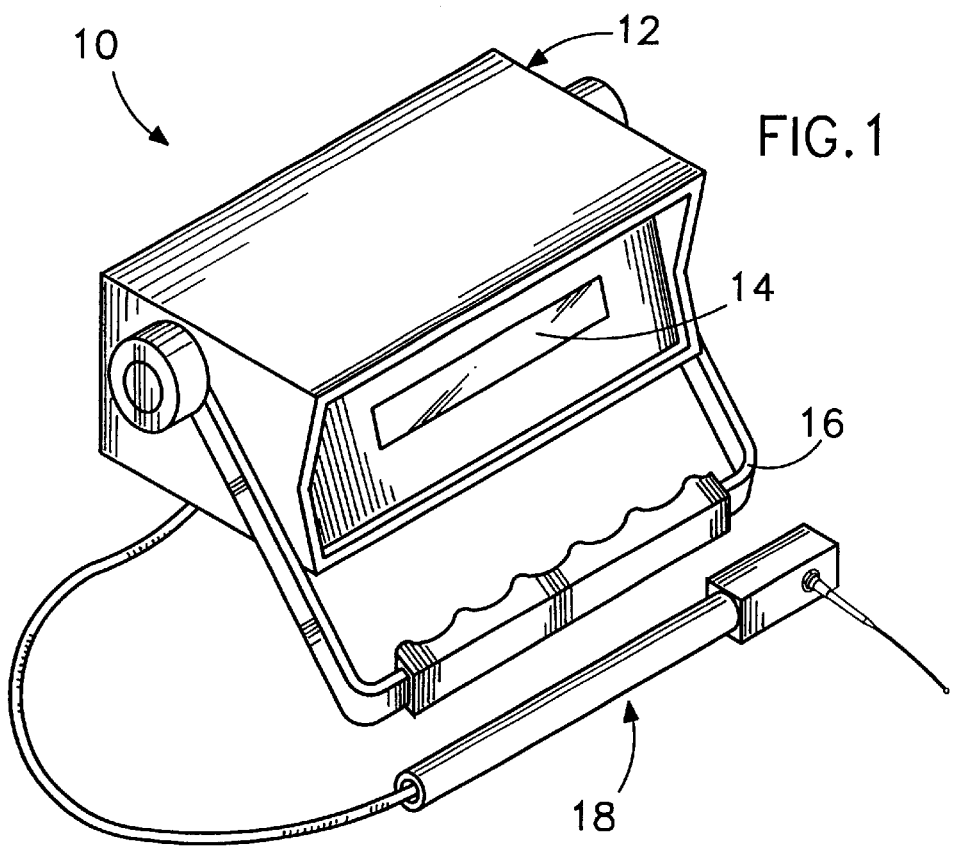
FIG. 1 is a perspective view of the present invention electronic algometer for measuring sensory thresholds in humans and animals.

Referring to FIG. 1, there is shown at 10 the present invention apparatus for measuring sensory thresholds in humans and laboratory animals. The apparatus 10 includes an electronic device 12 which is generally a conventional electronic algometer known in the art and operates on 110V or 220V AC power or DC power, such as batteries. The electronic algometer 12 has a digital readout display 14 for displaying the pressure in grams or other suitable unit of measurement and a handle 16 which is rotatably attached on opposite sides of the algometer 12 for carrying the device from place to place. Since the internal circuitry of the electronic algometer 12 are well known in the art, the description thereof will not be described.

The electronic algometer 12 works in any position and is extremely simple to operate. It employs two readouts, one is a live readout, which shows any pressure present at the test tip at anytime, the other readout is a "peak and hold" showing the maximum pressure applied to the tip prior to the reaction of the test subject, which may be audio or withdrawal of the extremity being tested. One single reset button makes the unit ready for the next test.

Referring to FIGS. 1, 2, 3, 4 and 5, the apparatus 10 further includes an elongated hollow probe housing 18 of approximate pencil length and configured with a generally rectangular shaped front head portion 20 and a generally cylindrical shaped rear handle portion 22. The probe housing 18 may be formed of molded plastic, metal or any suitable material known in the art. The head portion 20 houses a pressure sensitive measuring means, such as a strain gauge 26 which is conventional in the art. The head portion 20 has an aperture 24 which extends therethrough on one side 25. The rear handle portion 22 provides gripping means for a user to hold the probe housing 18 and houses electrical wires 28 therein which are electrically interconnected between the strain gauge 26 and the electronic algometer 12.

Figure 2:
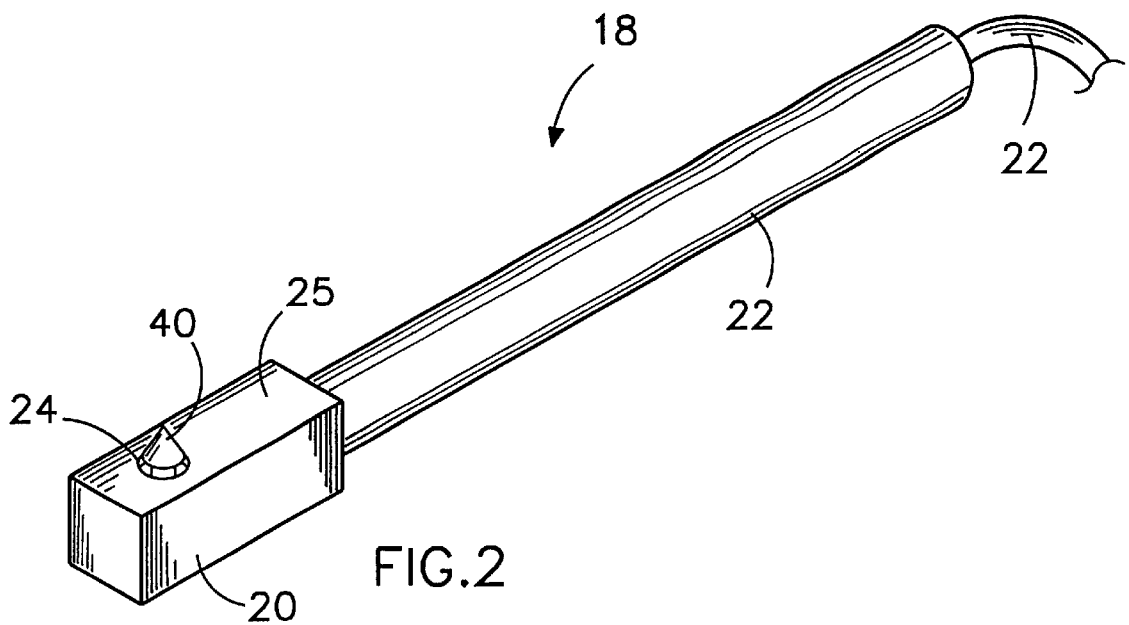
FIG. 2 is an enlarged perspective view of a probe housing of the present invention electronic algometer.
Figure 3:
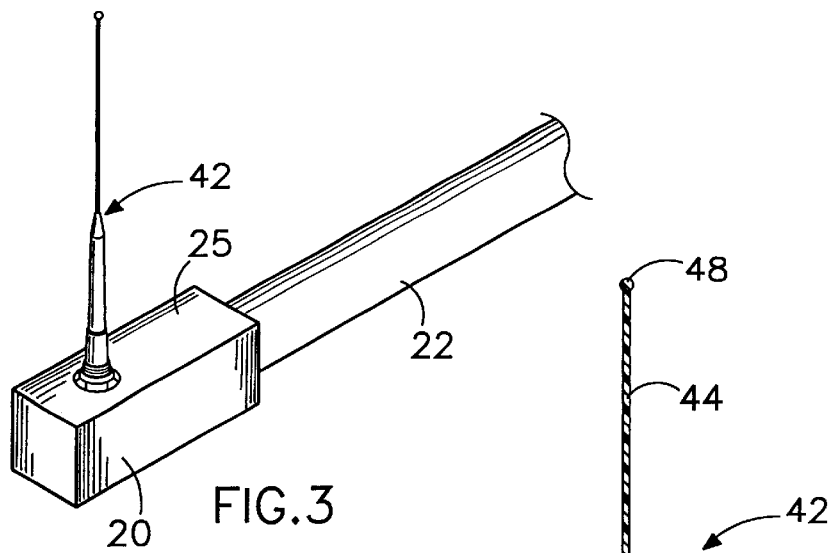
FIG. 3 is a perspective view a pressure probe assembly installed on the probe housing shown in FIG. 2.
Figure 4:
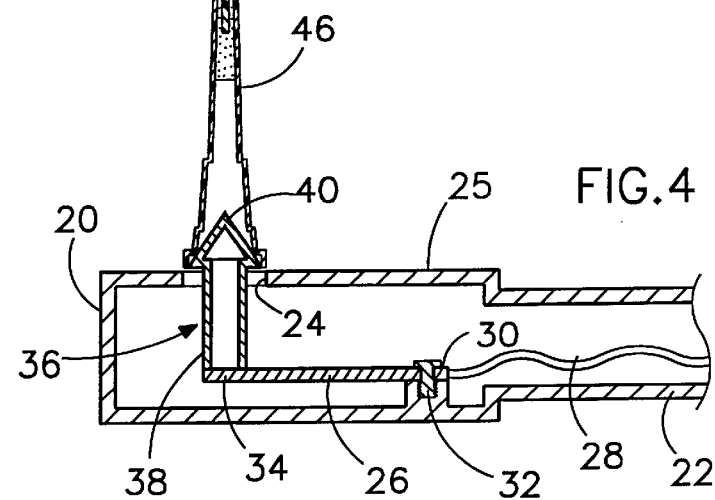
FIG. 4 is a partial longitudinal cross-sectional view taken through the probe housing and the pressure probe assembly shown in FIG. 3, showing no deflection on a strain gauge.
Figure 5:
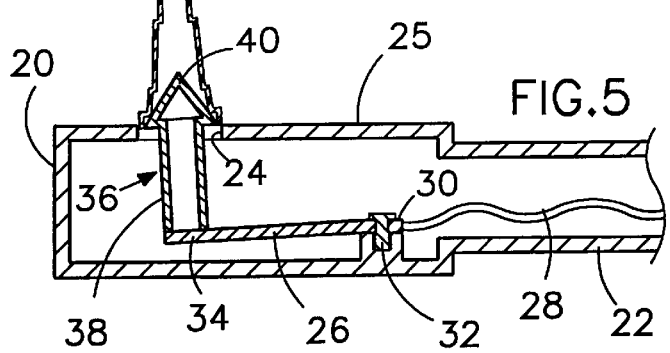
FIG. 5 is a partial longitudinal cross-sectional view taken through the probe housing and the pressure probe assembly shown in FIG. 3, showing deflection on the strain gauge.
Figure 6:
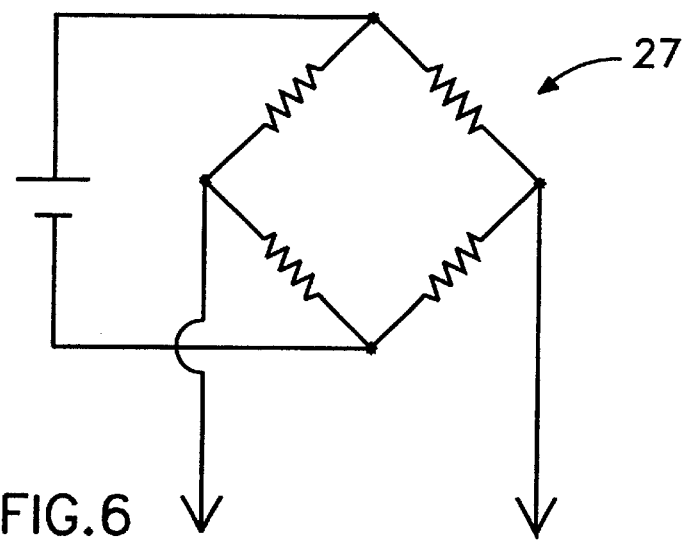
FIG. 6 is a simplified circuit diagram of the strain gauge.

Referring to FIGS. 2, 4 and 5, the strain gauge 26 has one end 30 fixed within the head portion 20 by a screw 32 or other suitable means and the other end 34 floating. A conventional strain gauge circuitry 27 is depicted in FIG. 6. A rigid support member 36 has a cylindrical portion 38 which is attached to the floating end 34 of the strain gauge 26 and a conical head portion 40 which extends through the aperture 24 on the head portion 20 of the probe housing 18. The aperture 24 has a diameter that is wide enough to allow the conical portion 40 of the rigid support member 36 to enter or exit the head portion 20 of the probe housing 18 without being too difficult.

Referring to FIGS. 3, 4, 5 and 7, there is shown at 42 a preferred pressure probe assembly which includes an elongated uniform resilient string or monofilament string 44 and an attachment member which can be a tapered hollow pipette member 46. The resilient string 44 is preferably made out of nylon material or any suitable material know to one skilled in the art and has one end inserted into an aperture provided on top of the hollow pipette member 46 and secured thereto by adhesive, glue or other suitable means while the other end is floating. By way of example, the resilient string 44 may be made out of polyethylene material or polypropylene material. The nylon string 44 has a uniform diameter of approximately in the range of 1.016 mm to 4.318 mm. The tapered hollow pipette member 46 is made out of plastic material and has a conventional internal luer-lock means for press fitting to the conical head portion 40 of the rigid support member 36.

A uniform tip diameter 48 is incorporated as part of the free end of the nylon string 44 for creating a uniform reaction when a force is exerted thereto. The uniform tip diameter 48 has a diameter of approximately in the range of 0.0500 mm to 4.000 mm; preferably the diameter of the uniform tip diameter is in the range of 0.80 mm to 0.850 mm.

The strain gauge 26 measures the amount of deflection responsive to the force applied from the nylon string 44 onto the rigid support member 36 with the uniform tip diameter 48 of the nylon string 44 (see FIG. 5) in contact with the skin area of the human or animal. The strain gauge 26 produces an electrical output signal indicative of the pressure applied. The electronic device 12 is electrically interconnected to the strain gauge 26 for receiving the electrical output signal from the strain gauge 26 and processing the output signal to accurately display the pressure applied by the uniform tip diameter 48 of the pressure probe assembly 42.

With the pressure probe assembly 42 and the electronic algometer 12, the user can read at any time the actual exerted force within 0.1 gram accuracy and not 40% change regardless of humidity or temperature. If the force changes today compared to yesterday by 40%, the user knows it and read it from the display of the electronic algometer 12 instead of blindly believing a number on a prior plastic handle that the user knows is changing anyway.

By combining the pressure probe assembly 42 from the 19–20 handles with the electronic algometer 12, the user is virtually independent of humidity and temperature changes, since the actual force is read from the readout display 14 of the electronic algometer 12 at anytime.

The combination of the electronic algometer 12 with the readout display and the pressure probe assembly 42 allows a user to see the change due to the degree of bending, humidity and temperature.

When the nylon strings are used, they have a certain limiting feature in them, so that beyond the maximum degree of bending and no bending at all they move within a certain gram range. A user simply cannot make more than a certain maximum with a given nylon string and the user takes the next stiffer one if required. This built-in limiting action of the flexible nylon strings is a major advantage over the prior art. They need almost no training of the user's hand.

Figure 7:
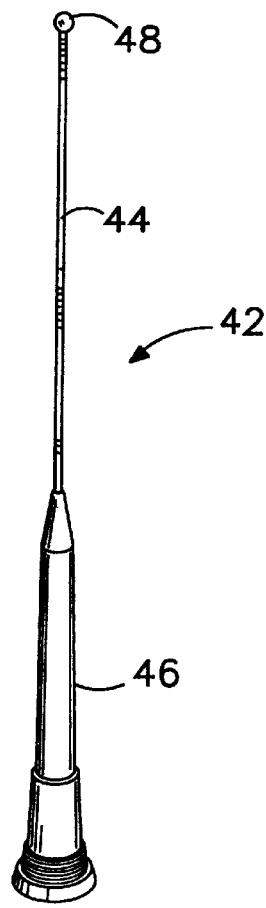
FIG. 7 is an enlarged perspective view of a preferred embodiment of the pressure probe assembly of the present invention.
Figure 8:
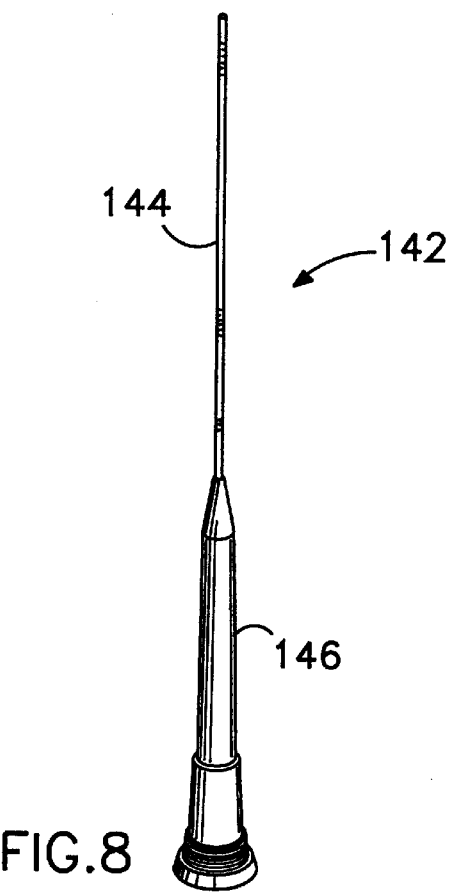
FIG. 8 is an enlarged perspective view of an alternative embodiment of the pressure probe assembly of the present invention.

Referring to FIG. 8, there is shown at 142 an alternative embodiment of a pressure probe assembly which includes an elongated resilient string or monofilament string 144 and a tapered hollow pipette member 146. In this embodiment, the pressure probe assembly 142 is similar to the embodiment described above except there is no uniform tip diameter 48 as shown in FIG. 7. The resilient string 144 is preferably made out of nylon material or any other suitable material known to one skilled in the art and has one end inserted into an aperture provided on top of the hollow pipette member 146 and secured thereto by adhesive, glue or other suitable means while the other end is floating. By way of example, the resilient string 142 may be made out of polyethylene material or polypropylene material. The nylon string 144 has a diameter of approximately in the range of 1.016 mm to 4.318 mm. The tapered hollow pipette member 146 is made out of plastic material and has a conventional internal luer-lock means for press fitting to the conical head portion 40 of the rigid support member 136. The pressure probe assembly 142 functions the same as the embodiment described above.

The concept of the nylon string 44 and tapered hollow pipette member 46 allows the combination to be interchangeable with a series of 19 to 20 different probes so that the amount of force in grams to be exerted by the nylon string on the subject can be varied, depending on the diameter of the nylon string used. Accordingly, the present invention includes a series of 19 to 20 different interchangeable nylon strings 44 and pipette members 46, where the pipette is the same to be interchangeably fitted onto the connecting head portion 40 of the rigid support member 36. The diameter of the nylon string varies from 1.016 mm for the lightest force to 4.316 mm to the heaviest force. In this way, when the lightest force diameter 1.016 mm is used and the subject does not feel any pressure or pain, then the next larger diameter nylon string is used, and so on until the subject can feel pain from the pressure exerted by the nylon string. It is a very novel feature of the present invention that all of the nylon strings, regardless of diameter, have the same uniform tip diameter so that a uniform reaction force from the subject is achieved when a force is exerted on the subject.

It will be appreciated that the dimensions described above are merely illustrative purposes only and it is also within the spirit and scope of the present invention to have other comparable sets of dimensions.

The present invention conforms to conventional forms of manufacture or any other conventional way known to one skilled in the art.

Defined in detail, the present invention is an apparatus for measuring sensory thresholds of a skin area of a human or animal, comprising: (a) a hollow probe housing having a front head portion with an opening therethrough and a rear handle portion for gripping the probe housing; (b) a strain gauge installed within the front head portion of the hollow probe housing and having one end fixed thereto and the other end movable; (c) a rigid support member attached to the movable end of the strain gauge and extending out from the opening of the front head portion of the probe housing; (d) a hollow pipette member removably press-fitted to the rigid support member; (e) an elongated resilient string made of nylon material having one end attached to the hollow pipette member, and the other end having a tip diameter for creating a reaction when a force is exerted thereto; (f) the strain gauge measuring the amount of deflection responsive to the force applied from the nylon string onto the rigid support member with the tip diameter of the nylon string in contact with the skin area of the human or animal and generating an electrical output signal indicative of the pressure applied; and (g) an electronic device electrically interconnected to the strain gauge for receiving the electrical output signal from the strain gauge, the electronic device including a digital readout display for displaying the pressure sensed by the strain gauge; (h) whereby the electronic device accurately displays the pressure applied by the uniform tip diameter of the nylon string on the skin area of the human or animal.

Defined broadly, the present invention is an apparatus for measuring sensory thresholds of a skin area of a human or animal, comprising: (a) a strain gauge having one end fixed and the other end movable; (b) a pipette member attached to the movable end of the strain gauge; (c) a resilient string having one end attached to the pipette member, and the other end having a tip diameter for creating a reaction when a force is exerted thereto; (d) the strain gauge measuring the amount of deflection responsive to the force applied from the resilient string onto the pipette member with the tip diameter of the resilient string in contact with the skin area of the human or animal and generating an electrical output signal indicative of the pressure applied; and (e) an electronic device electrically interconnected to the strain gauge for receiving the electrical output signal from the strain gauge, the electronic device including a readout display for displaying the pressure sensed by the strain gauge; (f) whereby the electronic device accurately displays the pressure applied by the tip diameter of the resilient string on the skin area of the human or animal.

Defined more broadly, the present invention is an apparatus for measuring sensory thresholds of a skin area of a human or animal, comprising: (a) a resilient string having one end attached to an attachment member, and the other end having a tip diameter for creating a reaction when a force is exerted thereto; (b) means for measuring the amount of deflection responsive to the force applied from the string onto the attachment member which is removably attached to the measuring means, with the tip diameter of the string in contact with the skin area of the human or animal and generating an electrical output signal to the measuring means indicative of the pressure applied; and (c) an electronic device electrically interconnected to the measuring means for receiving the electrical output signal, the electronic device including a display for displaying the pressure sensed by the measuring means; (d) whereby the electronic device accurately displays the pressure applied by the tip diameter of the resilient string on the skin area of the human or animal.

Defined alternatively in detail, the present invention is an apparatus for measuring sensory thresholds of a skin area of a human or animal, comprising: (a) a hollow probe housing having a front head portion with an opening therethrough and a rear handle portion for gripping the probe housing; (b) a strain gauge installed within the front head portion of the hollow probe housing and having one end fixed thereto and the other end movable; (c) a rigid support member attached to the movable end of the strain gauge and extending out from the opening of the front head portion of the probe housing; (d) a hollow pipette member removably press-fitted to the rigid support member; (e) an elongated resilient string made of nylon material having one end attached to the hollow pipette member, and the other end extending outwardly; (f) the strain gauge measuring the amount of deflection responsive to the force applied from the nylon string onto the rigid support member with the free end the nylon string in contact with the skin area of the human or animal and generating an electrical output signal indicative of the pressure applied; and (g) an electronic device electrically interconnected to the strain gauge for receiving the electrical output signal from the strain gauge, the electronic device including a digital readout display for displaying the pressure sensed by the strain gauge; (h) whereby the electronic device accurately displays the pressure applied by the nylon string on the skin area of the human or animal.

Defined alternatively broadly, the present invention is an apparatus for measuring sensory thresholds of a skin area of a human or animal, comprising: (a) a strain gauge having one end fixed and the other end movable; (b) a pipette member removably attached to the movable end of the strain gauge; (c) a resilient string having one end attached to the pipette member, and the other end extending outwardly; (d) the strain gauge measuring the amount of deflection responsive to the force applied from the string onto the pipette member with the free end of the string in contact with the skin area of the human or animal and generating an electrical output signal indicative of the pressure applied; and (e) an electronic device electrically interconnected to the strain gauge for receiving the electrical output signal from the strain gauge, the electronic device including a readout display for displaying the pressure sensed by the strain gauge; (f) whereby the electronic device accurately displays the pressure applied by the nylon string on the skin area of the human or animal.

Defined alternatively more broadly, the present invention is an apparatus for measuring sensory thresholds of a skin area of a human or animal, comprising: (a) a resilient string having one end attached to an attachment member and the other end free; (b) means for measuring the amount of deflection responsive to the force applied from the string onto the attachment member with the free end of the string in contact with the skin area of the human or animal and generating an electrical output signal indicative of the pressure applied; and (c) an electronic device electrically interconnected to the measuring means for receiving the electrical output signal, the electronic device including a display for displaying the pressure sensed by the measuring means; (d) whereby the electronic device accurately displays the pressure applied by the resilient string on the skin area of the human or animal.

Further defined in detail, the present invention is a pressure probe assembly used in conjunction with an electronic algometer for measuring sensory thresholds of a skin area of a human or animal, the electronic algometer having a hollow probe housing which houses a strain gauge and a support member extending through an opening on the probe housing, the pressure probe assembly comprising: (a) an attachment member being removably press-fitted to the support member; and (b) an elongated resilient string of selected standard length having one end inserted into and secured to the attachment member, and the other end free and having a uniform tip diameter for creating a uniform reaction when a force is exerted thereto; (c) whereby the strain gauge measures the amount of deflection responsive to the force applied from the resilient string onto the support member with the uniform tip diameter of the string in contact with the skin area of the human or animal and produces an electrical output signal indicative of the pressure applied.

Further defined broadly the present invention is a pressure probe assembly used in conjunction with an electronic pressure measuring device for measuring sensory thresholds of a skin area of a human or animal, the electronic device having a strain gauge, the pressure probe assembly comprising: (a) a pipette member being attachable to a movable end of the strain gauge; and (b) a resilient string having one end attached to the pipette member, and the other end having a tip for creating a uniform reaction when a force is exerted thereto; (c) whereby the strain gauge measures the amount of deflection responsive to the force applied from the resilient string onto the pipette member with the tip of the resilient string in contact with the skin area of the human or animal and produces an electrical output signal indicative of the pressure applied.

Further defined more broadly, the present invention is a probe assembly used in conjunction with electronic measuring means for measuring sensory thresholds of a skin area of a human or animal, the electronic measuring means having means for measuring the amount of deflection, the probe assembly comprising: (a) attachment mean being attachable to the measuring means; and (b) a resilient string having one end attached to the attachment means and the other end having a tip for creating a reaction when a force is exerted thereto; (c) whereby the measuring means measures the amount of deflection responsive to the force applied from the resilient string onto the attachment means with the tip of the resilient string in contact with the skin area of the human or animal and produces an electrical output signal indicative of the pressure applied.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. An apparatus for measuring sensory thresholds of a skin area of a human or animal, comprising:
    a. a hollow probe housing having a front head portion with an opening therethrough and a rear handle portion for gripping the probe housing;
    b. a strain gauge installed within said front head portion of said hollow probe housing and having one end fixed thereto and the other end movable;
    c. a rigid support member attached to the movable end of said strain gauge and extending out from said opening of said front head portion of said probe housing;
    d. a hollow pipette member removably press-fitted to said rigid support member;
    e. an elongated resilient string made of nylon material having one end attached to said hollow pipette member, and the other end having a tip diameter for creating a reaction when a force is exerted thereto;
    f. said strain gauge measuring the amount of deflection responsive to the force applied from said nylon string onto said rigid support member with said tip diameter of said nylon string in contact with said skin area of said human or animal and generating an electrical output signal indicative of the pressure applied; and
    g. an electronic device electrically interconnected to said strain gauge for receiving said electrical output signal from said strain gauge, the electronic device including a digital readout display for displaying the pressure sensed by said strain gauge;
    h. whereby said electronic device accurately displays the pressure applied by said uniform tip diameter of said nylon string on said skin area of said human or animal.

2. The apparatus in accordance with claim 1, wherein the diameter of said tip diameter of said nylon string is in a range of approximately 0.80 mm to 0.85 mm.

3. The apparatus in accordance with claim 1, wherein said electronic device includes an algometer.

4. The apparatus in accordance with claim 1, further comprising a series of hollow pipettes each respectively housing a resilient nylon string of a different diameter, but each nylon string having the same tip diameter.

5. The apparatus in accordance with claim 4, wherein said each resilient nylon string, regardless of its diameter, has the same uniform tip.

6. An apparatus for measuring sensory thresholds of a skin area of a human or animal, comprising:
    a. a strain gauge having one end fixed and the other end movable;
    b. a pipette member attached to said movable end of said strain gauge;
    c. a resilient string having one end attached to said pipette member, and the other end having a tip diameter for creating a reaction when a force is exerted thereto;
    d. said strain gauge measuring the amount of deflection responsive to the force applied from said resilient string onto said pipette member with said tip diameter of said resilient string in contact with said skin area of said human or animal and generating an electrical output signal indicative of the pressure applied; and e. an electronic device electrically interconnected to said strain gauge for receiving said electrical output signal from said strain gauge, the electronic device including a readout display for displaying the pressure sensed by said strain gauge;

f. whereby said electronic device accurately displays the pressure applied by said tip diameter of said resilient string on said skin area of said human or animal.

7. The apparatus in accordance with claim 6, further comprising a hollow probe housing having a front head portion with an opening therethrough and a rear handle portion for gripping the probe housing, where said strain gauge is installed in the front head portion such that said pipette member extends through the opening provided on the head portion.

8. The apparatus in accordance with claim 7, further comprising a rigid support member attached to the movable end of said strain gauge and extending out from said opening of said front head portion of said hollow probe housing, where said pipette member is press-fitted to said rigid support member.

9. The apparatus in accordance with claim 6, wherein the diameter of said tip diameter of said resilient string is in a range of approximately 0.05 mm to 4.0 mm.

10. The apparatus in accordance with claim 6, wherein said resilient string is made of nylon material.

11. The apparatus in accordance with claim 6, wherein said readout display is a digital readout.

12. The apparatus in accordance with claim 6, wherein said electronic device includes an electronic algometer.

13. The apparatus in accordance with claim 6, further comprising a series of hollow pipettes each respectively housing a resilient string of a different diameter, but each resilient string having the same tip diameter.

14. The apparatus in accordance with claim 13, wherein said each resilient string, regardless of its diameter, has the same uniform tip.

15. An apparatus for measuring sensory thresholds of a skin area of a human or animal, comprising:

a. a resilient string having one end attached to an attachment member, and the other end having a tip diameter for creating a reaction when a force is exerted thereto;

b. means for measuring the amount of deflection responsive to the force applied from said string onto said attachment member which is removably attached to the measuring means, with said tip diameter of said string in contact with said skin area of said human or animal and generating an electrical output signal to the measuring means indicative of the pressure applied; and c. an electronic device electrically interconnected to said measuring means for receiving said electrical output signal, the electronic device including a display for displaying the pressure sensed by said measuring means;

d. whereby said electronic device accurately displays the pressure applied by said tip diameter of said resilient string on said skin area of said human or animal.

16. The apparatus in accordance with claim 15, wherein the diameter of said tip diameter of said resilient string is in a range of approximately 0.05 mm to 4.0 mm.

17. The apparatus in accordance with claim 15, wherein said resilient string is nylon line made of nylon material.

18. The apparatus in accordance with claim 15, wherein said display is a digital readout.

19. The apparatus in accordance with claim 15, wherein said electronic device includes an electronic algometer.

20. The apparatus in accordance with claim 15, wherein said attachment member includes a pipette.

21. The apparatus in accordance with claim 15, further comprising a series of hollow pipettes each respectively housing a resilient string of a different diameter, but each resilient string having the same tip diameter.

22. The apparatus in accordance with claim 21, wherein said each resilient string, regardless of its diameter, has the same uniform tip.

23. An apparatus for measuring sensory thresholds of a skin area of a human or animal, comprising:

a. a hollow probe housing having a front head portion with an opening therethrough and a rear handle portion for gripping the probe housing;

b. a strain gauge installed within said front head portion of said hollow probe housing and having one end fixed thereto and the other end movable;

c. a rigid support member attached to the movable end of said strain gauge and extending out from said opening of said front head portion of said probe housing;

d. a hollow pipette member removably press-fitted to said rigid support member;

e. an elongated resilient string made of nylon material having one end attached to said hollow pipette member, and the other end extending outwardly;

f. said strain gauge measuring the amount of deflection responsive to the force applied from said nylon string onto said rigid support member with the free end said nylon string in contact with said skin area of said human or animal and generating an electrical output signal indicative of the pressure applied; and g. an electronic device electrically interconnected to said strain gauge for receiving said electrical output signal from said strain gauge, the electronic device including a digital readout display for displaying the pressure sensed by said strain gauge;

h. whereby said electronic device accurately displays the pressure applied by said nylon string on said skin area of said human or animal.

24. The apparatus in accordance with claim 23, wherein said electronic device includes an electronic algometer.

25. The apparatus in accordance with claim 23, further comprising a series of hollow pipettes each respectively housing a resilient nylon string of a different diameter, but each nylon string having the same tip diameter.

26. The apparatus in accordance with claim 25, wherein said each resilient nylon string, regardless of its diameter, has the same uniform tip.

27. An apparatus for measuring sensory thresholds of a skin area of a human or animal, comprising:

a. a strain gauge having one end fixed and the other end movable;

b. a pipette member removably attached to said movable end of said strain gauge;

c. a resilient string having one end attached to said pipette member, and the other end extending outwardly;

d. said strain gauge measuring the amount of deflection responsive to the force applied from said string onto said pipette member with the free end of said string in contact with said skin area of said human or animal and generating an electrical output signal indicative of the pressure applied; and e. an electronic device electrically interconnected to said strain gauge for receiving said electrical output signal from said strain gauge, the electronic device including a readout display for displaying the pressure sensed by said strain gauge;

f. whereby said electronic device accurately displays the pressure applied by said resilient string on said skin area of said human or animal.

28. The apparatus in accordance with claim 27, further comprising a hollow probe housing having a front head portion with an opening therethrough and a rear handle portion for gripping the probe housing, where said strain gauge is installed in the front head portion such that said pipette member extends through the opening provided on the head portion.

29. The apparatus in accordance with claim 27, further comprising a rigid support member attached to the movable end of said strain gauge and extending out from said opening of said front head portion of said hollow probe housing, where said pipette member is press-fitted to said rigid support member.

30. The apparatus in accordance with claim 27, wherein said resilient string is a nylon line made of nylon material.

31. The apparatus in accordance with claim 27, wherein said readout display is a digital readout.

32. The apparatus in accordance with claim 27, wherein said electronic device includes an electronic algometer.

33. The apparatus in accordance with claim 28, further comprising a series of hollow pipettes each respectively housing a resilient string of a different diameter, but each resilient string having the same tip diameter.

34. The apparatus in accordance with claim 27, wherein said each resilient string, regardless of its diameter, has the same uniform tip.

35. An apparatus for measuring sensory thresholds of a skin area of a human or animal, comprising:

a. a resilient string having one end attached to an attachment member and the other end free;

b. means for measuring the amount of deflection responsive to the force applied from said string onto said attachment member with said free end of said string in contact with said skin area of said human or animal and generating an electrical output signal indicative of the pressure applied; and c. an electronic device electrically interconnected to said measuring means for receiving said electrical output signal, the electronic device including a display for displaying the pressure sensed by said measuring means;

d. whereby said electronic device accurately displays the pressure applied by said resilient string on said skin area of said human or animal.

36. The apparatus in accordance with claim 35, wherein said resilient string is a nylon line made of nylon material.

37. The apparatus in accordance with claim 35, wherein said display is a digital readout.

38. The apparatus in accordance with claim 35, wherein said electronic device includes an electronic algometer.

39. The apparatus in accordance with claim 35, wherein said measuring means includes a strain gauge.

40. The apparatus in accordance with claim 35, wherein said attachment member includes a pipette.

41. The apparatus in accordance with claim 40, further comprising a series of hollow pipettes each respectively housing a resilient string of a different diameter, but each resilient string having the same uniform tip.

42. A pressure probe assembly used in conjunction with an electronic algometer for measuring sensory thresholds of a skin area of a human or animal, the electronic algometer having a hollow probe housing which houses a strain gauge and a support member extending through an opening on the probe housing, the pressure probe assembly comprising:

a. an attachment member being removably press-fitted to said support member; and b. an elongated resilient string of selected standard length having one end inserted into and secured to said attachment member, and the other end free and having a uniform tip diameter for creating a uniform reaction when a force is exerted thereto;

c. whereby said strain gauge measures the amount of deflection responsive to the force applied from said resilient string onto said support member with said uniform tip diameter of said resilient string in contact with said skin area of said human or animal and produces an electrical output signal indicative of the pressure applied.

43. The pressure probe assembly in accordance with claim 42, further comprising a series of hollow pipettes each respectively housing a resilient nylon string of a different diameter, but each nylon string having the same uniform tip diameter.

44. The pressure probe assembly in accordance with claim 43, wherein said each nylon string, regardless of its diameter, has the same uniform tip.

45. The pressure probe assembly in accordance with claim 44, wherein the diameter of said uniform tip of said nylon string is in a range of approximately 0.050 mm to 4.00 mm.

46. A pressure probe assembly used in conjunction with an electronic pressure measuring device for measuring sensory thresholds of a skin area of a human or animal, the electronic device having a strain gauge, the pressure probe assembly comprising:

a. a pipette member being attachable to a movable end of said strain gauge; and b. a resilient string having one end attached to said pipette member, and the other end having a tip for creating a uniform reaction when a force is exerted thereto;

c. whereby said strain gauge measures the amount of deflection responsive to the force applied from said resilient string onto said pipette member with said tip of said resilient string in contact with said skin area of said human or animal and produces an electrical output signal indicative of the pressure applied.

47. The pressure probe assembly in accordance with claim 46, wherein the diameter of said tip of said resilient string is in a range of approximately 0.05 mm to 4.0 mm.

48. The pressure probe assembly in accordance with claim 46, wherein said resilient string is made of nylon material.

49. A probe assembly used in conjunction with electronic measuring means for measuring sensory thresholds of a skin area of a human or animal, the electronic measuring means having means for measuring the amount of deflection, the probe assembly comprising:

a. attachment means being attachable to said measuring means; and b. a resilient string having one end attached to said attachment means and the other end having a tip for creating a reaction when a force is exerted thereto;

c. whereby said measuring means measures the amount of deflection responsive to the force applied from said resilient string onto said attachment means with said tip of said resilient string in contact with said skin area of said human or animal and produces an electrical output signal indicative of the pressure applied.

50. The probe assembly in accordance with claim 49, wherein the diameter of said tip of said resilient string is in a range of approximately 0.05 mm to 4.0 mm.

51. The probe assembly in accordance with claim 49, wherein said resilient string is a nylon line made of nylon material.

52. The probe assembly in accordance with claim 49, wherein said attachment means includes a hollow pipette member.

53. The probe assembly in accordance with claim 49, further comprising a series of hollow pipettes each respectively housing a resilient string of a different diameter, but each resilient string having the same tip diameter.

54. The probe assembly in accordance with claim 53, wherein said each resilient string, regardless of its diameter, has the same uniform tip.

* * * * *